(12) United States Patent
Veirman et al.

(10) Patent No.: US 8,571,812 B2
(45) Date of Patent: Oct. 29, 2013

(54) METHOD FOR MAPPING OXYGEN CONCENTRATION

(75) Inventors: Jordi Veirman, Annecy le Vieux (FR); Sebastien Dubois, Scionzier (FR); Nicolas Enjalbert, Burlats (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 13/818,744

(22) PCT Filed: Aug. 30, 2011

(86) PCT No.: PCT/FR2011/000482
§ 371 (c)(1),
(2), (4) Date: Feb. 25, 2013

(87) PCT Pub. No.: WO2012/028791
PCT Pub. Date: Mar. 8, 2012

(65) Prior Publication Data
US 2013/0158889 A1 Jun. 20, 2013

(30) Foreign Application Priority Data

Sep. 2, 2010 (FR) .................................... 10 03510

(51) Int. Cl.
*G01N 25/00* (2006.01)
*G06F 19/00* (2011.01)
*G06F 17/40* (2006.01)

(52) U.S. Cl.
USPC ............... 702/32; 73/866; 324/451; 324/719; 374/45; 702/23; 702/24; 702/26; 702/30; 702/127

(58) Field of Classification Search
USPC .............. 73/432.1, 865.8, 866; 205/775, 782, 205/785.5; 324/71.1, 71.4, 71.5, 451, 452, 324/459, 464, 468, 470, 600, 649, 691, 693, 324/719; 340/500, 540, 635, 657; 374/15, 374/45, E11.001; 429/90; 438/14; 702/1, 702/22, 23, 24, 26, 30, 32, 57, 81, 127, 187, 702/189; 708/100, 105, 200
IPC ........... G01D 21/00; G01N 25/00,27/00, 27/02, G01N 27/041; G06F 11/00, 11/30, 11/32, G06F 17/00, 17/40, 19/00
See application file for complete search history.

(56) References Cited

U.S. PATENT DOCUMENTS 2,782,369 A * 2/1957 Werner et al. ................. 324/701
2,859,407 A * 11/1958 Henisch .................... 324/754.21

(Continued)

FOREIGN PATENT DOCUMENTS

EP 0 020 993 A1 1/1981

OTHER PUBLICATIONS

Thurber et al., "Resistivity-Dopant Density Relationship for Phosphorus-Doped Silicon," *Journal of the Electrochemical Society*, Aug. 1980, pp. 1807-1812, vol. 127, No. 8.

(Continued)

*Primary Examiner* — Edward Cosimano
(74) *Attorney, Agent, or Firm* — Oliff & Berridge, PLC

(57) ABSTRACT

A method for determining the oxygen concentration of a sample made of a semiconductor material includes a heat treatment step of the sample to form thermal donors, the measurement of the resistivity in an area of the sample, the determination of the thermal donor concentration from a relation expressing the charge carrier mobility according to an ionized dopant impurity concentration, by adding to the dopant impurity concentration four times the thermal donor concentration, and from the measured resistivity value. The method finally includes determining the oxygen concentration from the thermal donor concentration.

8 Claims, 5 Drawing Sheets

(56) References Cited

U.S. PATENT DOCUMENTS

| | | | | |
|---|---|---|---|---|
| 2,943,984 | A | * | 7/1960 | Gullett ............................ 205/782 |
| 2,993,846 | A | * | 7/1961 | Tyler ............................... 205/782 |
| 3,134,077 | A | * | 5/1964 | Hutchins, IV ..................... 330/2 |
| 3,233,174 | A | * | 2/1966 | Mcaleer et al. ................. 324/693 |
| 3,487,301 | A | * | 12/1969 | Yeh et al. ....................... 324/717 |
| 3,495,170 | A | * | 2/1970 | Biard et al. .................... 324/719 |
| 3,628,137 | A | * | 12/1971 | Mazur ............................ 324/717 |
| 4,344,815 | A | | 8/1982 | Cazarra et al. |
| 4,429,047 | A | * | 1/1984 | Jastrzebski et al. ................ 436/4 |
| 5,096,839 | A | * | 3/1992 | Amai et al. ...................... 438/16 |
| 5,373,804 | A | * | 12/1994 | Tachimori et al. ............... 117/13 |
| 5,385,115 | A | * | 1/1995 | Tomioka et al. .................. 117/2 |
| 5,485,803 | A | * | 1/1996 | Habu .............................. 117/14 |
| 7,078,919 | B2 | * | 7/2006 | Prussin .......................... 324/719 |
| 2005/0052191 | A1 | * | 3/2005 | Prussin .......................... 324/719 |

OTHER PUBLICATIONS

Ulyashin et al., "Characterization of the oxygen distribution in Czochralski silicon using hydrogen-enhanced thermal donor formation," *Materials Science and Engineering B*, 2000, pp. 124-129, vol. 73, Elsevier Science S.A.

Arora et al., "Electron and Hole Mobilities in Silicon as a Function of Concentration and Temperature," *IEEE Transactions on Electron Devices*, 1982, pp. 292-295, vol. ED-29, No. 2, IEEE.

Londos et al., "Effect of oxygen concentration on the kinetics of thermal donor formation in silicon at temperatures between 350 and 500 °C.," *Appl. Phys. Lett.*, Mar. 29, 1993, pp. 1525-1526, vol. 62, No. 13, American Institute of Physics.

Mar. 5, 2013 International Preliminary Report on Patentability issued in International Patent Application No. PCT/FR2011/000482 (with partial English translation).

Translation of Nov. 18, 2011 International Search Report issued in International Patent Application No. PCT/FR2011/000482.

* cited by examiner

METHOD FOR MAPPING OXYGEN CONCENTRATION

BACKGROUND OF THE INVENTION

The invention relates to a method enabling to map the oxygen concentration of a semiconductor sample.

STATE OF THE ART

Silicon substrates intended for the microelectronics industry or for photovoltaic applications generally contain oxygen. When they are not in the form of precipitates, oxygen atoms occupy interstitial positions in the crystal lattice. In the case of single-crystal silicon, obtained by the Czochralski method, or in the case of solar-grade polycrystalline silicon, the oxygen concentration varies between $10^{17}$ and $2\times10^{18}$ atoms/$cm^3$.

The interstitial oxygen ($O_i$) has a significant impact on the mechanical and electric properties of silicon. In particular, at temperatures ranging between 350° C. and 500° C., the oxygen forms precipitates called thermal double donors (TDD) which modify the electric properties of the material by creating free electrons. At higher temperature, the oxygen forms other precipitates enabling to trap metal impurities present in the silicon. A getter effect can thus be obtained. Further, oxygen improves the mechanical properties of substrates by blocking the dislocations introduced by manufacturing processes.

For photovoltaic applications, a high oxygen concentration causes a performance decrease, especially a decrease in the conversion efficiency of photovoltaic cells based on silicon doped with boron (B).

Knowing the oxygen distribution within the substrate thus appears to be important, to locally determine the influence of oxygen on the electric and mechanical properties of silicon. This information then enables to optimize crystallization or device manufacturing methods.

The oxygen concentration of a sample is conventionally determined by Fourier transform infrared (FTIR) spectroscopy. However, this technique is slow and lacks accuracy. It further requires a preparation of the sample surface.

Article "Characterization of the oxygen distribution in Czochralski silicon using hydrogen-enhanced thermal donor formation" (A. G. Ulyashin et al., Materials Science and Engineering B73 124-129, 2000) describes another technique for determining the oxygen concentration.

This technique is based on the formation of TDD thermal donors. A hydrogen plasma enhanced heat treatment is applied to a p-type sample to form a p-n junction. Then, the depth of the p-n junction in the sample is determined by means of SRP-type (spreading resistance probe) resistance measurements or C-V (capacitance-voltage) capacitance measurements. The thermal donor concentration is then calculated from the depth of the p-n junction. A mathematical model enables to determine the oxygen concentration from the thermal donor concentration.

The characterization methods used require, just as the FTIR, a preparation of the sample. The SRP characterization requires beveling the sample to establish the resistance profile all throughout the sample depth. The C-V characterization uses metal contacts at the sample surface. Such contacts are difficult to remove without damaging or contaminating the sample material.

Due to the complexity of such characterization methods, the measurement technique of the above-mentioned article is slow and difficult to apply to substrates of microelectronic and photovoltaic industries.

Further, preparation and hydrogenation of the substrate make it impossible to use at the end of the measurement.

SUMMARY OF THE INVENTION

A need therefore exists to provide a method that is fast and simple to implement, enabling to determine the oxygen concentration of a sample from the thermal donor concentration.

This need tends to be satisfied by the steps of:

a) submitting the sample to a heat treatment to form thermal donors, b) measuring the resistivity in an area of the sample, c) determining the thermal donor concentration from:

a relation expressing the mobility of charge carriers according to an ionized dopant impurity concentration, by adding to the ionized dopant impurity concentration four times the thermal donor concentration, and the measured resistivity value.

After determining the oxygen concentration, a step of heat treatment at a temperature greater than or equal to 650° C. is further provided to restore the sample in its initial state.

BRIEF DESCRIPTION OF THE DRAWINGS

Other advantages and features will become more clearly apparent from the following description of particular embodiments of the invention given for non-restrictive example purposes only and represented in the appended drawings, in which.

DESCRIPTION OF A PREFERRED EMBODIMENT OF THE INVENTION

It is provided a method enabling to determine oxygen concentration $C_o$ of a silicon substrate from a measurement of electric resistivity ρ. Indeed, resistivity is one of the electric parameters affected by the generation of thermal donors (TDD) originating from oxygen.

The resistivity varies according to two parameters: concentration m of free charge carriers and mobility μ of these carriers. Its general expression is:

$$\rho = \frac{1}{m \cdot q \cdot \mu} \quad (1)$$

q being the elementary charge (q=1.6×10$^{-19}$ C).

Submitting the substrate to a temperature ranging between 350° C. and 500° C. will cause the generation of thermal donors. Free electrons are thus created in the substrate, which generates a variation of the charge carrier concentration and thus a resistivity variation.

The resistivity measurement after a heat treatment thus enables to quantify this charge carrier concentration variation and to deduce thermal donor concentration $N_{TDD}$ and, later, oxygen concentration $C_o$.

To obtain more accurate results, the influence of thermal donors on mobility has been determined. In particular, a new model of mobility $\mu(N_{TDD})$, which takes into account thermal donor concentration $N_{TDD}$, has been developed.

Figure 1:
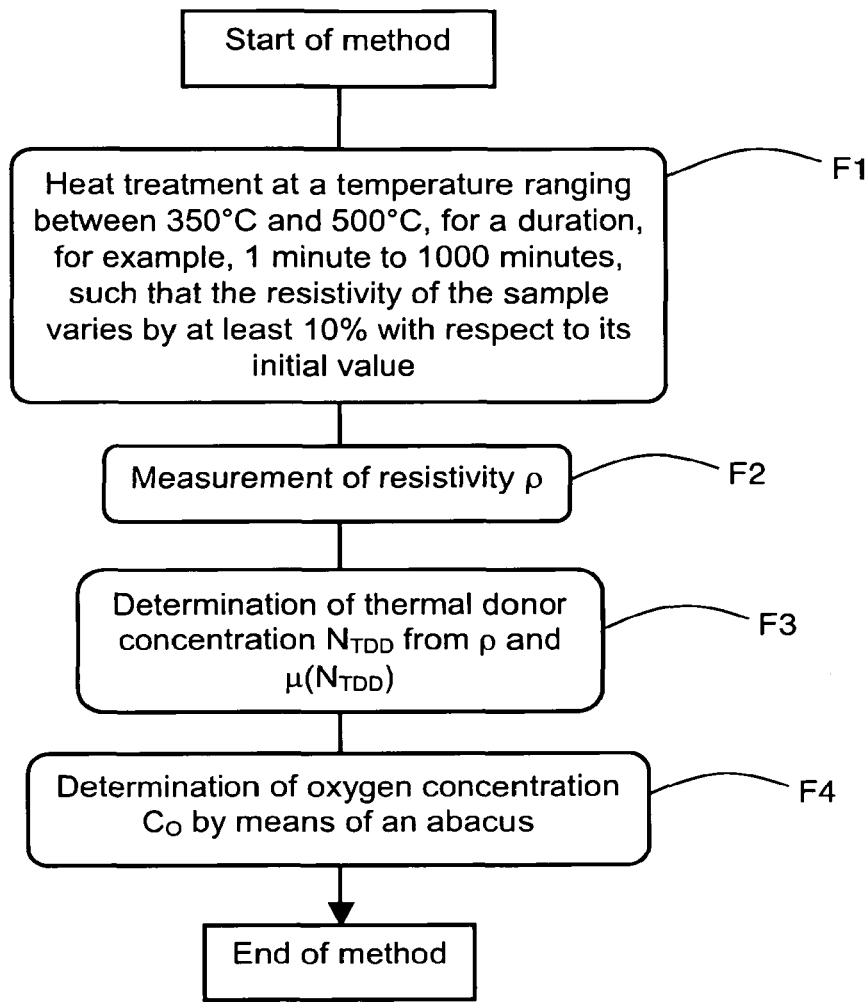
FIG. 1 represents steps of a method for determining oxygen concentration $C_o$ according to the present invention.

FIG. 1 represents steps F1 to F4 of a method for determining oxygen concentration $C_o$.

In a first step F1, a silicon substrate containing oxygen is submitted to a heat treatment, or annealing, to form thermal donors. The annealing temperature preferably ranges between 350° C. and 500° C. Indeed, as will be described hereafter, the kinetics of the formation of thermal donors is well known in this range of temperatures, especially at 450° C.

At a step F2, the resistivity is measured in a target area of the substrate. This measurement may be simply performed by the four-point probe method.

The next step (F3) consists in calculating thermal donor concentration $N_{TDD}$ from this resistivity measurement. To achieve this, relation (1) is used and relations describing free carrier concentration m and mobility μ according to concentration $N_{TDD}$ are used.

This new mathematical model is detailed hereafter.

In a p-type doped substrate, the majority charge carriers are holes. Their number is defined by the amount of dopant impurities implanted in the silicon, generally boron atoms (B). Such atoms are called electron acceptors. The majority charge carrier concentration is then equal to the boron concentration: m=[B].

Conversely, in an n-type substrate, the majority charge carriers are electrons. The dopant impurities are electron donor atoms, for example, phosphorus atoms (P). It implies: m=[P].

Further, there exist so-called "compensated" substrates, which have both types of dopant impurities. In this case, the majority charge carrier concentration will be equal to:
m=[B]−[P] if the substrate is p-type,
m=[P]−[B] if the substrate is n-type.

After the heat treatment, each thermal donor releases two electrons. The majority charge carrier concentration varies as follows:

| | | |
|---|---|---|
| for the n-type substrate: m = [P] + 2*$N_{TDD}$ | (2), and |
| for the p-type substrate: m = [B] − 2*$N_{TDD}$ | (3). |

For a compensated substrate, there will be:

| | |
|---|---|
| m = [P] − [B] + 2*$N_{TDD}$ | (2'), for an n-type substrate, |
| m = [B] − [P] − 2*$N_{TDD}$ | (3'), for a p-type substrate. |

Thus, after forming the thermal donors TDD, the electron concentration is increased by twice concentration $N_{TDD}$ for an n-type substrate. In a p-type substrate, the hole concentration is decreased by twice concentration $N_{TDD}$ after a rebalancing of the charges.

Mobility μ represents the ability of charge carriers to move in a material under the action of an electric field. The mobility in a single-crystal silicon free of metal impurities and of dislocations has been the subject of many studies.

In particular, article "Electron and Hole Mobilities in Silicon as a Function of Concentration and Temperature" (Arora N. D. et al., IEEE transactions on electron devices, vol. ED-29, no. 2, p. 292, 1982) describes the mobility of electrons and of holes according to the dopant concentration and to temperature T.

It may be expressed by the following relation:

$$\mu(T, N_{A/D}) = \mu_{min} T_n^{\beta 1} + \frac{(\mu_{max} - \mu_{min}) T_n^{\beta 2}}{1 + \left(\frac{N_{A/D}}{N_{ref} T_n^{\beta 3}}\right)^{\alpha T_n^{\beta 4}}}, \quad (4)$$

Tn is the temperature normalized with respect to the ambient temperature (Tn=T/300). NA, respectively ND, is the concentration in acceptor, respectively donor, ionized dopant impurities (for example, boron or phosphorus). Parameters $\mu_{max}$, $\mu_{min}$, $N_{ref}$, α, β1, β2, β3, β4 are given for the two types of charge carriers in Table 1 hereafter for silicon.

TABLE 1

| Majority carriers in Si | $\mu_{max}$ (cm$^2$· V$^{-1}$· s$^{-1}$) | $\mu_{min}$ (cm$^2$· V$^{-1}$· s$^{-1}$) | $N_{ref}$(cm$^{-3}$) | α | β1 | β2 | β3 | β4 |
|---|---|---|---|---|---|---|---|---|
| Electrons | 1417 | 60 | 9.64 × 10$^{16}$ | 0.664 | −0.57 | −2.33 | 2.4 | −0.146 |
| Holes | 470 | 37.4 | 2.82 × 10$^{17}$ | 0.642 | −0.57 | −2.33 | 2.4 | −0.146 |

The first term of expression (4) reflects the dependence of mobility to temperature T, due to microvibrations (called phonons) induced by the temperature rise. The second term reflects the influence of ionized dopant impurities $N_A$ and/or $N_D$, which hinder the displacement of charge carriers.

However, this expression does not take into account the presence of thermal donors, which are also dopant impurities and thus disturb mobility measurements.

The inventors have established a new expression of mobility by adapting expression (4) to silicon containing thermal donors.

Thermal donors are also considered as ionized impurities. Unlike one-time ionized boron or phosphorus atoms, thermal donors are ionized twice during the annealing step (two electrons per TDD). The ability of a dopant impurity to hinder the displacement of charge carriers is called scattering power. The scattering power of an n-time ionized atoms is equal to n$^2$. In the case of a thermal donor, it is thus equal to 4.

The influence of a thermal donor on mobility thus is 4 times greater than that of an acceptor or donor atom. Thus, to express mobility as a function of thermal donors, expression (4) of mobility is modified by adding four times thermal donor concentration $N_{TDD}$ to dopant impurity concentration $N_D$ and/or $N_A$.

Expression (4) becomes:

$$\mu(T, N_{A/D}, N_{TDD}) = \mu_{min}T_n^{\beta 1} + \frac{(\mu_{max} - \mu_{min})T_n^{\beta 2}}{1 + \left(\frac{N_{A/D} + 4 \times N_{TDD}}{N_{ref}T_n^{\beta 3}}\right)^{\alpha T_n^{\beta 4}}}, \quad (5)$$

with $N_{A/D}=N_A$ or $N_D$ or $N_A+N_D$ according to the type of substrate.

A relation of mobility in a doped single-crystal silicon comprising thermal donors is thus obtained. This new relation is preferably used to determine thermal donor concentration $N_{TDD}$. Indeed, equation (1)

$$\rho(N_{TDD}) = \frac{1}{m(N_{TDD}) \cdot q \cdot \mu(N_{TDD})}$$

may be solved based on the resistivity value obtained at step F3.

Step F4 of the method of FIG. 1 enables to determine oxygen concentration $C_O$ by means of charts when thermal donor concentration $N_{TDD}$ is known. To form such charts, it is necessary to look deeper into the thermal donor forming phenomenon.

Article "Effect of oxygen concentration on the kinetics of thermal donor formation in silicon at temperatures between 350 and 500° C." (Londos C. A. et al., Appl. Phys. Lett. 62 (13), pp. 1525, 1993) describes the kinetics of thermal donor formation in silicon, for temperatures ranging between 350° C. and 500° C. More specifically, the article shows that the thermal donor forming speed strongly depends on the oxygen concentration.

The results of this study have enabled to establish charts of thermal donor concentration $N_{TDD}$ according to duration t of the heat treatment, for different values of oxygen concentration $C_o$.

Figure 2:
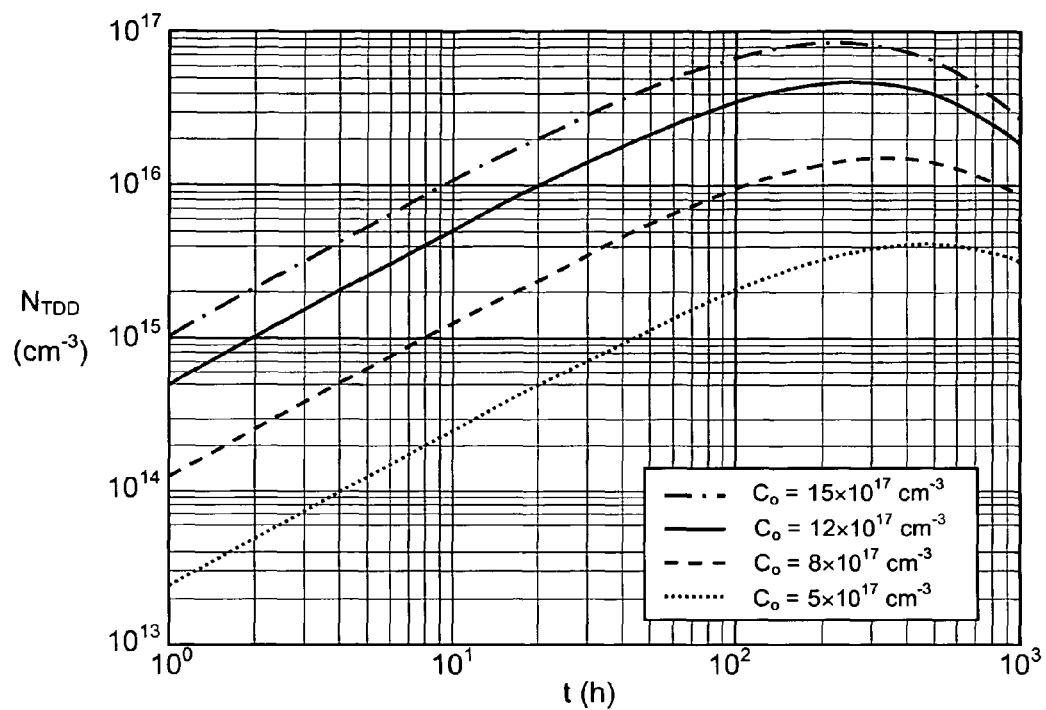
FIG. 2 represents charts of thermal donor concentration $N_{TDD}$ according to duration t of the heat treatment, for different values of oxygen concentration $C_o$.

FIG. 2 shows one of these charts, for an annealing temperature on the order of 450° C. Actually, this temperature is a good compromise between the thermal donor generation speed and the maximum obtained concentration. A temperature higher than 450° C. favors the TDD forming speed to the detriment of the maximum concentration. A high temperature should thus be preferred when the oxygen concentration is assumed to be high, for example greater than $5 \times 10^{17}$ cm$^{-3}$. Conversely, a temperature smaller than 450° C. will enable to increase the maximum TDD concentration and may be used for substrates having a low approximate oxygen concentration, for example, smaller than $5 \times 10^{17}$ cm$^{-3}$.

It can be observed in FIG. 2 that a small variation of oxygen concentration $C_o$ causes a strong variation of thermal donor concentration $N_{TDD}$. As an example, after one hour of annealing, a substrate having an oxygen concentration equal to $5 \times 10^{17}$ cm$^{-3}$ forms $2.5 \times 10^{13}$ TDD per cm$^{-3}$, while a substrate with three times as large an oxygen concentration forms approximately 100 times more thermal donors.

The abacus of FIG. 2 enables to determine the measured value of oxygen concentration $C_o$ in the substrate area, for a given concentration $N_{TDD}$ and a given annealing duration t.

To increase the accuracy of the oxygen concentration determination method, it is preferable for the annealing to last for a sufficiently long time to create a resistivity variation of at least 10%. Indeed, such a variation is easily measurable.

Figure 3:
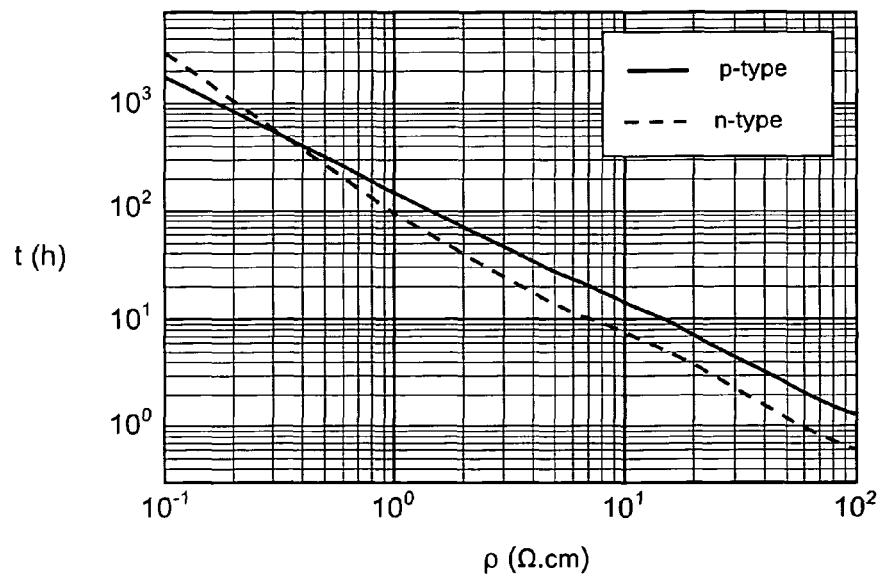
FIG. 3 represents, according to initial resistivity ρ, heat treatment duration t necessary to obtain a 10% variation of the resistivity, for an n-type substrate and a p-type substrate.

FIG. 3 represents, for a p-type substrate and an n-type substrate, annealing duration t at 450° C. necessary to observe a 10% variation between initial resistivity ρ, shown in abscissas, and the value measured after annealing. These curves will preferably be used to determine a minimum annealing duration. This duration preferably ranges between 1 minute and 1000 minutes.

The calculation of $N_{TDD}$ performed at step F3 by means of equations (1), (2) (or (2'), (3), (3')), and (5) also requires knowing the value of dopant impurity concentration $N_A$ and/or $N_D$. This value is generally given by the substrate supplier. If not, it may be determined in an additional step of the method of FIG. 1.

Figure 4:
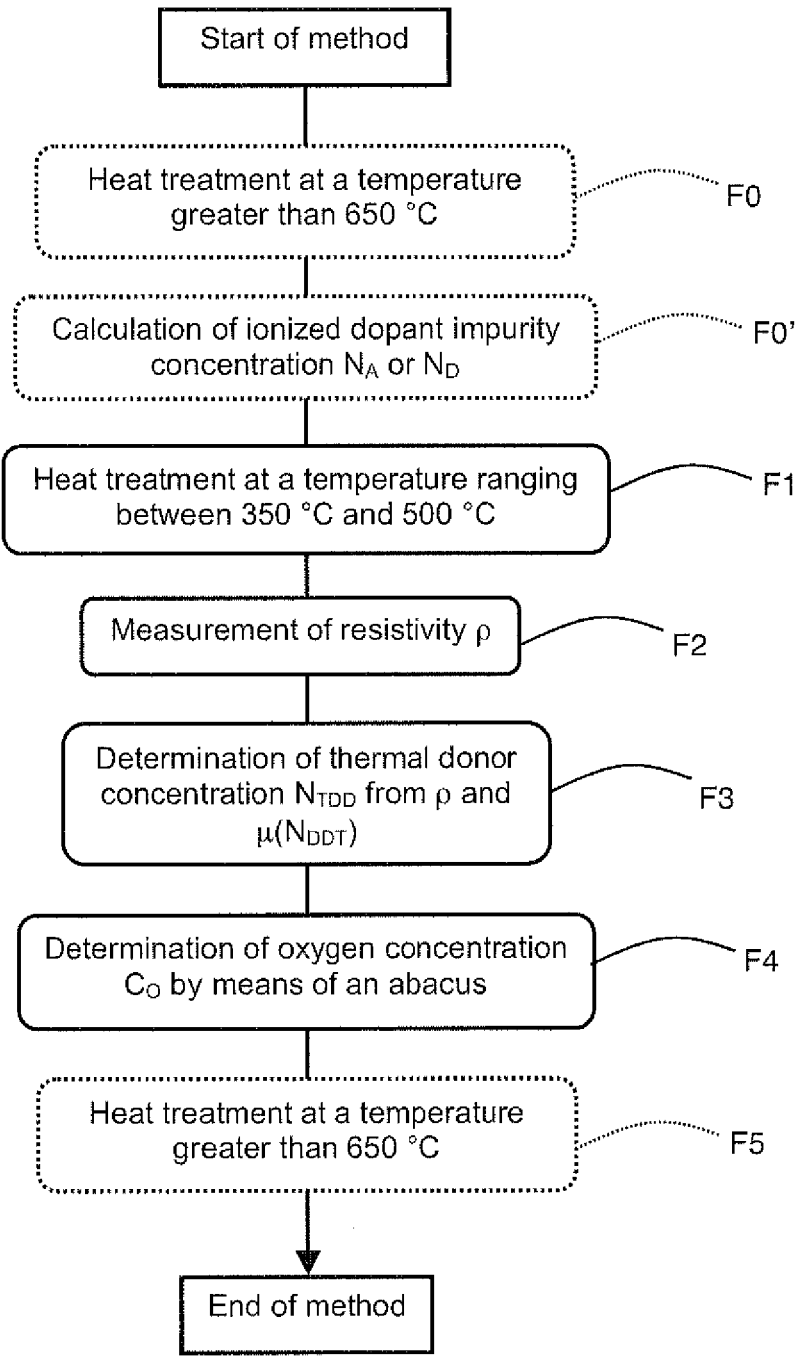
FIG. 4 represents additional steps of the determination method of FIG. 1.

FIG. 4 shows additional steps of the determination method, one of which enables to determine dopant impurity concentration $N_A$ or $N_D$.

When concentration $N_A$ or $N_D$ is unknown, the initial resistivity of the substrate may be measured before annealing at a step F0'. This measurement then enables to calculate dopant impurity concentration $N_A$ or $N_D$.

In the case of a compensated substrate, concentration $N_A-N_D$ is obtained. Thus, to access $N_A$ and $N_D$, either at least one value should be known from the manufacturer, or additional GDMS-type (Glow Discharge Mass Spectroscopy) measurements should be performed.

To make sure that the substrate comprises no thermal donors in its initial state, which could distort the value of $N_A$ or $N_D$, an annealing is preferably performed, at F0, at a temperature greater than or equal to 650° C. This makes oxygen precipitates (or thermal donors TDD) unstable and eliminates them. Oxygen atoms then return to their interstitial positions.

Annealing F0 may be performed even when concentration $N_A$ or $N_D$ is known.

Such an annealing is preferably also used at the end of the process, at F5, after having determined the oxygen concentration in the desired area (F4). Thanks to annealing step F5, the substrate returns to its initial state and may be used again.

The determination method shown in FIG. 1 may advantageously be applied in several areas of the substrate, to perform a full mapping thereof. Such a mapping may then be used to optimize the device manufacturing.

Figure 5:
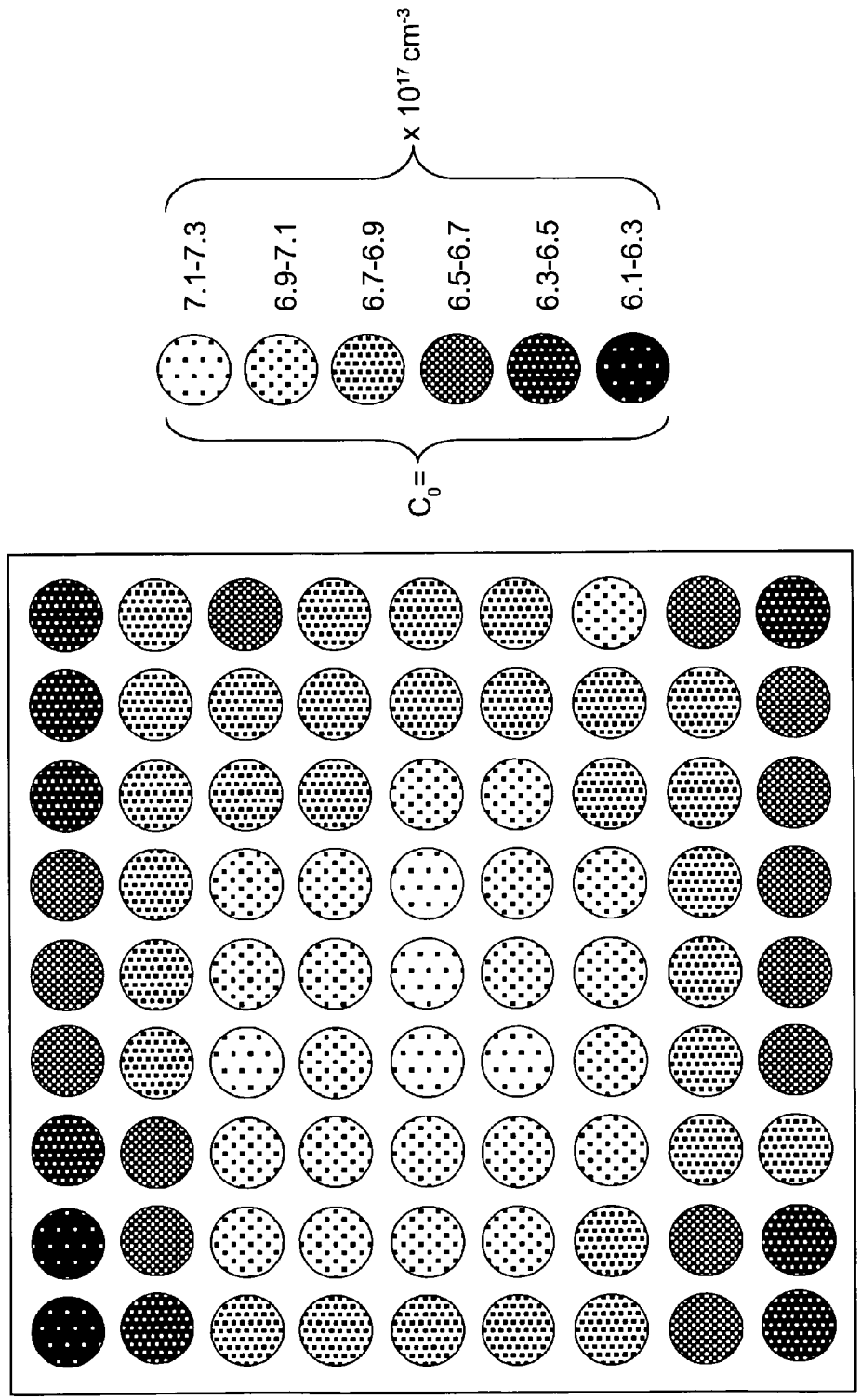
FIG. 5 represents a mapping of oxygen concentration $C_o$ obtained by means of the method of FIG. 1.

FIG. 5 schematically represents an oxygen mapping obtained by means of the measurement method. The substrate used is made of phosphorus-doped silicon (n-type) and initially comprises no thermal donors. Its initial resistivity is close to 18 Ω·cm. The oxygen concentration varies between $6.1 \times 10^{17}$ cm$^{-3}$ and $7.1 \times 10^{17}$ cm$^{-3}$.

The mathematical model used gives a good sensitivity to the determination method, due to the strong dependence between thermal donor concentration $N_{TDD}$ and oxygen concentration $C_o$. Further, the resistivity characterization is simple to perform and fast. It uses a low-cost standard characterization tool, and may be applied at a large scale. The determination method has an accuracy on the order of 1% and a spatial resolution of approximately 60 μm.

Figure 6:
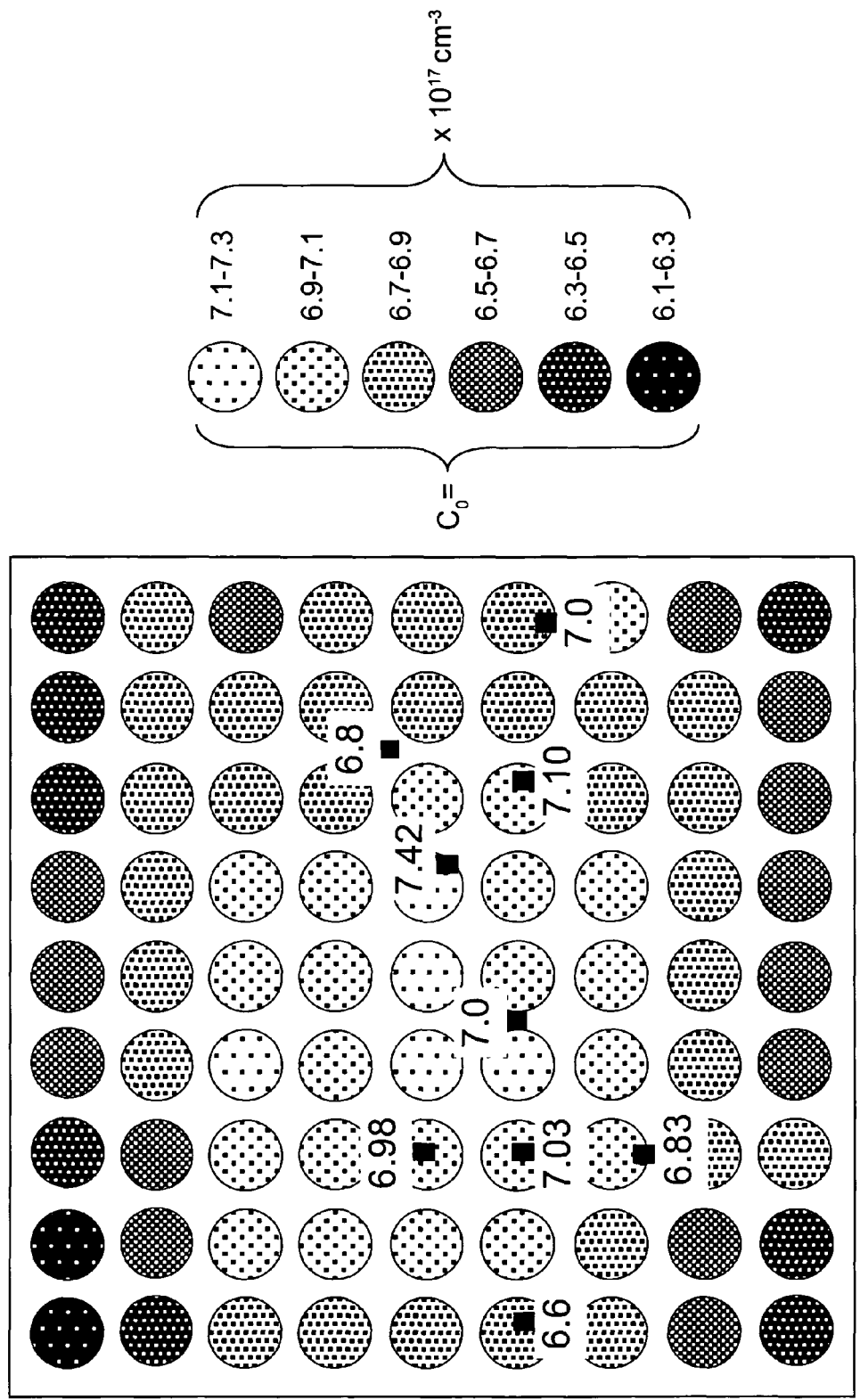
FIG. 6 represents values of the oxygen concentration obtained by infrared spectroscopy (FTIR) compared with the mapping of FIG. 5.

FIG. 6 shows values of oxygen concentration $C_o$ obtained by means of the conventional FTIR technique in several areas of the substrate, marked with black squares. The mapping of FIG. 5 has been reproduced as a comparison. A good correspondence between the values obtained by the determination method and those of the FTIR technique can be observed, in terms of absolute values as well as of variations at the substrate scale.

Many variants and modifications of the determination method described herein will occur to those skilled in the art. The method has been described in relation with a silicon substrate. However, the method may also be applied to germanium or silicon-germanium substrates. Indeed, germanium also is a semiconductor where thermal donors may be formed in the presence of oxygen. A germanium-specific mobility model will then be used as a starting point, after which it will be adapted by adding four times thermal donor concentration $N_{TDD}$ to dopant impurity concentration $N_A$ and/or $N_D$.

What is claimed is:

1. A method for determining the oxygen concentration of a sample made of a semiconductor material comprising the steps of:
    a) submitting the sample to a heat treatment to form thermal donors,
    b) measuring the resistivity in an area of the sample,
    c) determining the thermal donor concentration from:
        a relation expressing the mobility of charge carriers according to an ionized dopant impurity concentration by adding to the ionized dopant impurity concentration four times the thermal donor concentration, and
        the measured resistivity value, and
    d) determining the oxygen concentration of the sample from the thermal donor concentration.

2. The method according to claim 1, wherein the relation expressing mobility is written as:

$$\mu = \mu_{min} T_n^{\beta 1} + \frac{(\mu_{max} - \mu_{min}) T_n^{\beta 2}}{1 + \left(\frac{N_{A/D} + 4 \times N_{TDD}}{N_{ref} T_n^{\beta 3}}\right)^{\alpha T_n^{\beta 4}}},$$

where:
    Tn is equal to T/300, T being temperature,
    NA/D is the ionized dopant impurity concentration of the sample,
    NTDD is the thermal donor concentration,
    α, β1, β2, β3, β4, μmax, μmin, Nref are constant parameters according to the nature of the charge carriers.

3. The method according to claim 1, comprising, after having determined the oxygen concentration, a step of heat treatment at a temperature greater than or equal to 650° C.

4. The method according to claim 1, wherein steps b) and c) are repeated in several areas of the sample to perform a mapping.

5. The method according to claim 1, wherein the heat treatment has a duration such that the resistivity of the sample varies by at least 10% with respect to its initial value.

6. The method according to claim 5, wherein the duration of the heat treatment ranges between 1 minute and 1000 minutes.

7. The method according to claim 1, initially comprising a step of heat treatment at a temperature greater than or equal to 650° C.

8. The method according to claim 7, comprising determining the dopant impurity concentration of the sample by a resistivity measurement.

* * * * *